United States Patent
Fishburne, Jr.

(10) Patent No.: US 8,323,021 B2
(45) Date of Patent: Dec. 4, 2012

(54) DENTAL BILATETAL BITE BLOCK

(75) Inventor: Cotsworth P. Fishburne, Jr., Rockhill, SC (US)

(73) Assignee: Centrix, Inc., Shelton, CT (US)

( * ) Notice: Subject to any disclaimer, the term of this patent is extended or adjusted under 35 U.S.C. 154(b) by 172 days.

(21) Appl. No.: 12/592,451

(22) Filed: Nov. 25, 2009

(65) Prior Publication Data

US 2010/0129767 A1      May 27, 2010

Related U.S. Application Data

(60) Provisional application No. 61/118,358, filed on Nov. 26, 2008.

(51) Int. Cl.
*A61C 5/00*       (2006.01)
*A61B 1/24*       (2006.01)

(52) U.S. Cl. .......................................... 433/140; 433/30

(58) Field of Classification Search ............... 433/30–31, 433/136, 140; 600/189, 246–248, 237–238; 128/862
See application file for complete search history.

(56) References Cited

U.S. PATENT DOCUMENTS

| | | | |
|---|---|---|---|
| 735,762 A | 8/1903 | Hare | |
| 1,010,147 A * | 11/1911 | Ivory | 433/138 |
| 2,574,217 A * | 11/1951 | Lundgren et al. | 433/31 |
| 2,823,455 A | 4/1956 | Sprague | |
| 2,937,445 A | 10/1956 | Erickson | |
| 3,468,030 A * | 9/1969 | Nivison et al. | 433/136 |
| 4,179,815 A | 12/1979 | Hoffman | 433/140 |
| 4,511,329 A | 4/1985 | Diamond | 433/31 |
| 4,550,986 A * | 11/1985 | Leach | 359/883 |
| 4,852,143 A * | 7/1989 | Scheier et al. | 433/136 |
| 5,009,595 A | 4/1991 | Osborn | 433/140 |
| 5,222,000 A * | 6/1993 | Adler | 359/847 |
| 6,241,521 B1 * | 6/2001 | Garrison | 433/140 |
| 6,267,591 B1 | 7/2001 | Barstow | 604/358 |
| 6,517,549 B1 | 2/2003 | Dennis | 606/108 |
| 6,634,884 B2 | 10/2003 | Phillips | 433/138 |
| 7,425,664 B2 | 9/2008 | Maass, Jr. et al. | 604/358 |
| 2005/0277085 A1 * | 12/2005 | Coleton | 433/31 |
| 2006/0142718 A1 * | 6/2006 | Maass et al. | 604/370 |

* cited by examiner

*Primary Examiner* — Heidi M Eide
(74) *Attorney, Agent, or Firm* — Fattibene and Fattibene, LLC; Paul A. Fattibene

(57) ABSTRACT

A sheet of material having a central body portion with attached wings capable of folding towards each other on either side. The wings of the bite block fold toward each other along fold lines adjacent the central body portion and provide a structure for biting down upon for propping the mouth of a patient open during a dental procedure. A mirrored surface may be placed on the central body portion for improving visibility in the mouth. The bite block also holds or retracts the tongue and cheeks away from a work area in the mouth. The wings protect the cheeks as well as provide improved visibility within the mouth. Additionally, moisture control within the mouth is improved. The bite block may be made inexpensively and is disposable.

15 Claims, 8 Drawing Sheets

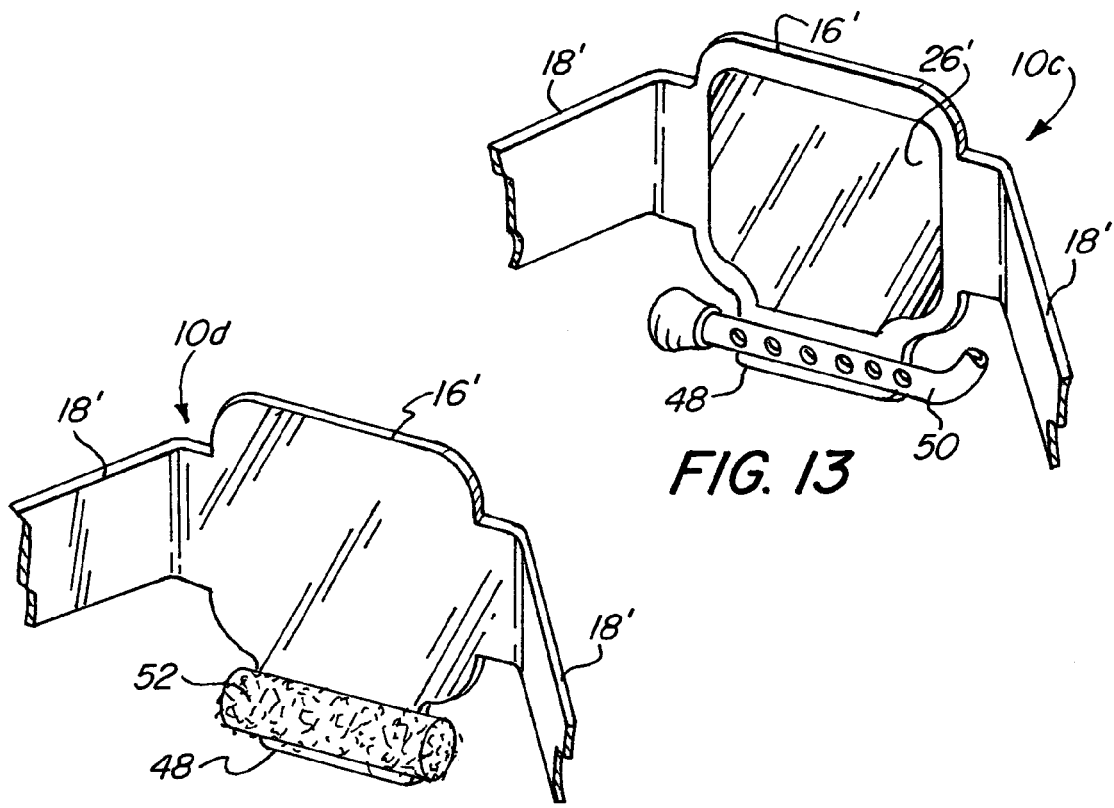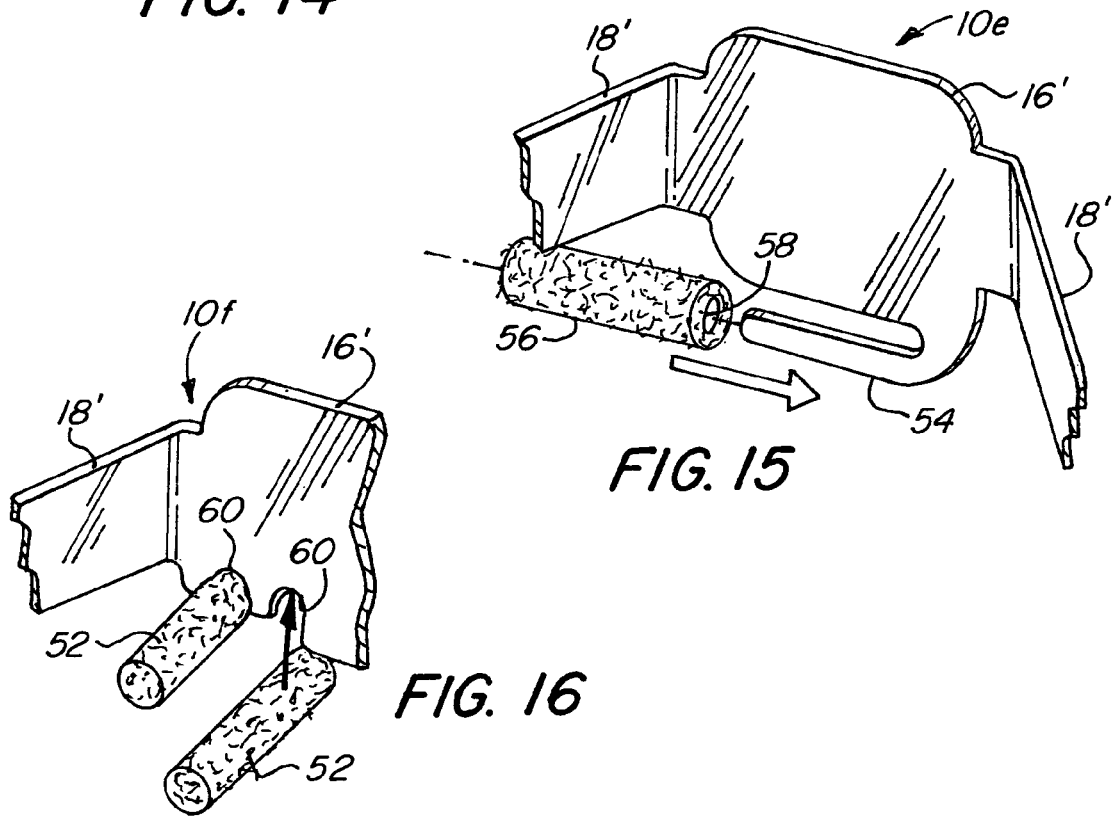

DENTAL BILATETAL BITE BLOCK

RELATED APPLICATION

This application claims the benefit of U.S. Provisional Application No. 61/118,358 filed Nov. 26, 2008

FIELD OF THE INVENTION

The invention relates in general, to dental appliances, and, in particular, to mouth props, also known as bite blocks, to keep the mouth open during dental procedures.

BACKGROUND OF THE INVENTION

Dental mouth props, or bite blocks, are devices which are inserted into the patient's mouth between the upper and lower teeth to keep the mouth opened in a relatively fixed position. This allows access to the interior of the mouth for dental procedures including but not limited to such aspects of dental treatment as phophys, endo, ortho, perio and restorative work.

Bite blocks provide for more efficiency and ease of performance by the dental professional as they provide the dental professional with some measure of control over the size of the opening of the mouth. Bite blocks provide comfort to the typical patient as they can relax the muscles in the jaw as they rest their teeth on the block. This is particularly beneficial in longer duration dental procedures.

A bit block is disclosed in U.S. Pat. No. 4,179,815 entitled "Dental Device" and issuing to Hoffman on Dec. 25, 1979. Therein disclosed is a dental device having a body, bite block portions, and a tongue shield restricting movement of the tongue towards the lingual surface of the teeth.

Another dental device is disclosed in U.S. Pat. No. 4,511,329 entitled "Moisture Controlling Lingual Dental Mirror" and issuing to Diamond on Apr. 16, 1985. Therein disclosed is a tongue holder and support for a check retractor that provides moisture control and has a mirror for viewing the lingual surface of the lower dentition.

Another dental device is disclosed in U.S. Pat. No. 6,267,591 entitled "Dental Prop, Throat Dam and Retractor" and issuing to Barstow on Jul. 31, 2001. Therein disclosed is a tongue retracting surface, a throat dam and an integral lip retracting surface with a grip portion. A prop portion has angled biting surfaces adapted to engage the teeth. A reflective material is attached to the tongue retracting surface.

While these prior dental devices have performed their intended function in aiding dental procedures, they are relatively large and expensive to manufacture. Additionally, they have to be sterilized between patients to prevent the possibility of cross contamination. Therefore, there is a need for a simple inexpensive bite block that provides improved visibility within the confines of a patient's mouth.

SUMMARY OF THE INVENTION

The present invention comprises a dental bite block for use in dental procedures and in general medical or cosmetic procedures that require access to the interior of a subject's or patient's mouth. The bite block provides a comfortable prop for the patient to rest his teeth upon, with the mouth in an open position. In a preferred embodiment, a bite block comprises a symmetrical body portion having flexible wings on either side with increasing width extending from the body portion. The bite block may be made of a composite or structured material having a mirror finish on one surface, a foam core, and a smooth white paper on the opposing surface. Fold lines may be scored adjacent the body portion for angling the flexible wings to fit a patient's mouth.

Other embodiments of the bite block comprise a symmetrical structure with a center body portion capable of retracting the tongue, where the center body portion tapers into two symmetrical saddles that allow the resting of the upper and lower row of teeth upon the saddles.

Embodiments additionally comprise wings attached to the saddles wherein the wings can be flexible to provide adjustment. The patient can also bite into the junction of the saddle and its wings.

Additional embodiments comprise reflective or mirrored surfaces on the center body portion which provide a dental professional with a view of the interior, lingual, or back side of teeth and gums as well as increased illumination.

Illumination can be provided for by reflection of ambient light, light directed into the mouth, or from light sources attached to the bite block.

Further embodiments comprise an absorptive material capable of removing saliva from the interior cavity of the mouth. Additionally, embodiments comprise suction devices that, when connected to air vacuum systems typically found in dental offices, can provide suction for the removal of amounts of saliva, blood, and other residual fluids and particulates that may accumulate in the mouth during a dental procedure.

Additional embodiments can comprise any of the following structures. A dental apparatus described herein where the mouth props are bilateral, enabling quick and easy placement. A dental apparatus described herein where the mouth props are thin, allowing for more working room in the mouth. A dental apparatus described herein where the bilateral mouth props complement each other, resulting in stability. A dental apparatus incorporating bilateral bite blocks that distribute muscle stress evenly to both sides of the mouth. A dental apparatus described herein that supports a mirror of glass, plastic based, or stainless steel that shows the lingual surfaces of the maxillary or mandibular anterior teeth. A dental apparatus supporting a mirror that can be angled, both vertically and horizontally, so as to show the lingual surfaces of many teeth in the mouth, maxillary and mandibular, anterior and posterior. A dental apparatus as described above, whose mirror can illuminate the teeth and areas of the mouth mentioned above. A dental apparatus described as above whose mirror is shaped, whereby the lower part of the mirror extends in length down from the center of the mirror, allowing more vision of the lower or mandibular teeth and allowing the operator to invert the entire device when vision of the lingual services of the upper or maxillary teeth is desirable. A dental apparatus having a mirror when made of a plastic material, it can be coated with an anti-fogging surface. A dental apparatus as described above that anchors both a regular mirror on one side and a magnifying mirror on the other side. A dental apparatus may have a body with an incorporated or attached illumination source. A dental apparatus as described above that affords a method of tongue retraction. A dental apparatus as described above that decreases the amount of moisture in the anterior floor of the mouth through its tongue retracting ability. A dental apparatus as described above which increases the amount of work area behind the maxillary or mandibular anterior teeth by in tongue retracting ability. A dental apparatus as described above which has wings attached which facilitate the placement of the device and prevent its being swallowed. A device as described above that has wings attached that provide intraoral cheek retraction. A device as described above that has wings that provide lip retraction.

It is an object of the present invention to improve visibility in the mouth during a dental procedure.

It is another object of the present invention to provide tongue retraction.

It is yet a further object of the present invention to provide an inexpensive disposable device.

It is an advantage of the present invention that the wings are adjustable to accommodate different size mouths.

It is an advantage of the present invention that it may be placed in the mouth independent of orientation.

It is a feature of the present invention that it is symmetrical in both the longitudinal axis and the lateral axis.

It is a feature of the present invention that a mirror or highly reflective surface is used on one side.

It is another feature of the present invention that it has flexible wings.

It is yet another feature of the present invention that it has a composite structure with a foam core.

These and other objects, advantages, and features will become more readily apparent in view of the following more detailed description.

BRIEF DESCRIPTION OF THE DRAWINGS

FIG. 13 is a schematic view illustrating a body portion having a vacuum line attached of an embodiment of the present invention.

FIG. 14 is a schematic view illustrating a body portion having a cotton roll attached of an embodiment of the present invention.

FIG. 15 is a schematic view illustrating a body portion having an arm for attaching a cotton roll of an embodiment of the present invention.

FIG. 16 is a schematic view illustrating an arm portion having indents for receiving a cotton roll of an embodiment of the present invention.

DETAILED DESCRIPTION OF THE PREFERRED EMBODIMENTS

Providing a means to maintain a fairly consistent opening of the mouth can be of benefit to dental and medical professionals while performing various dental and oral procedures, hereinafter generally called dental procedures. The natural response of the patient is to want to close the mouth, as protracted sessions with an open mouth can become tiring and cause fatigue to the related muscles of the jaw.

Provided for herein is an apparatus and means for maintaining a relative consistent opening of the mouth while reducing fatigue to the patient. Additionally, tongue retraction can be had, as well as removal of excess fluids such as saliva. Further, a mirrored surface can be used as well which provide for a view of interior portions of teeth, gums, and the general mouth.

Figure 1A:
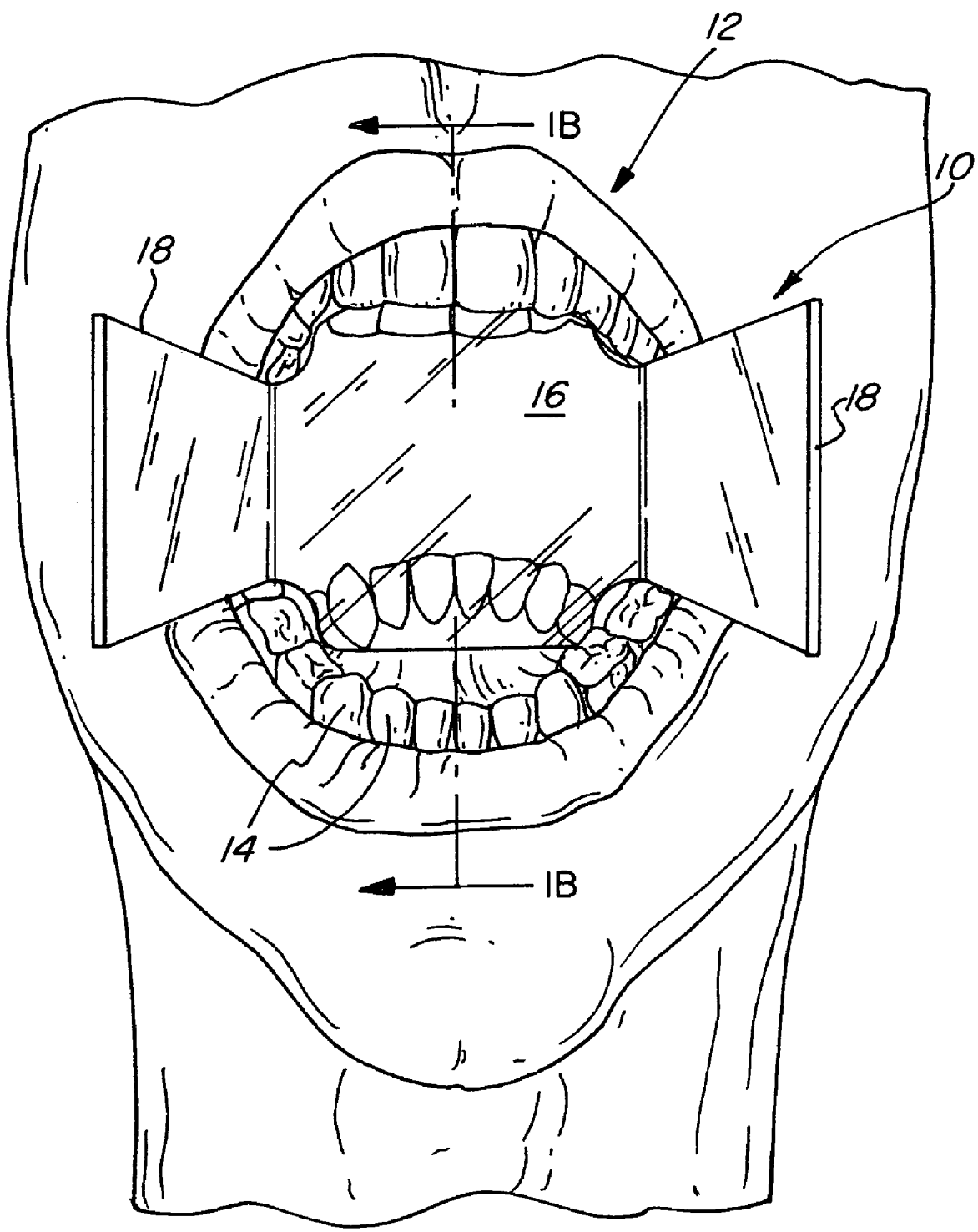
FIG. 1A is a front schematic view illustrating placement of an embodiment of the present invention in a patient's mouth.

FIG. 1A illustrates a front view of an embodiment of the present invention placed in the mouth of a patient. A bite block 10 has is placed in the mouth 12 for holding the teeth 14 and keeping the mouth 12 open. The bite block 10 has a center body portion 16 and wings 18 extending from either side of the body portion 16. The teeth 14 are blocked open by the wings 18. The wings 18 may be angularly disposed relative to the plane of the body portion 16. The body portion 16 and wings 18 may have a mirror or highly reflective surface thereon to improve visibility and imaging of the back of the front teeth or the lingual area.

Figure 1B:
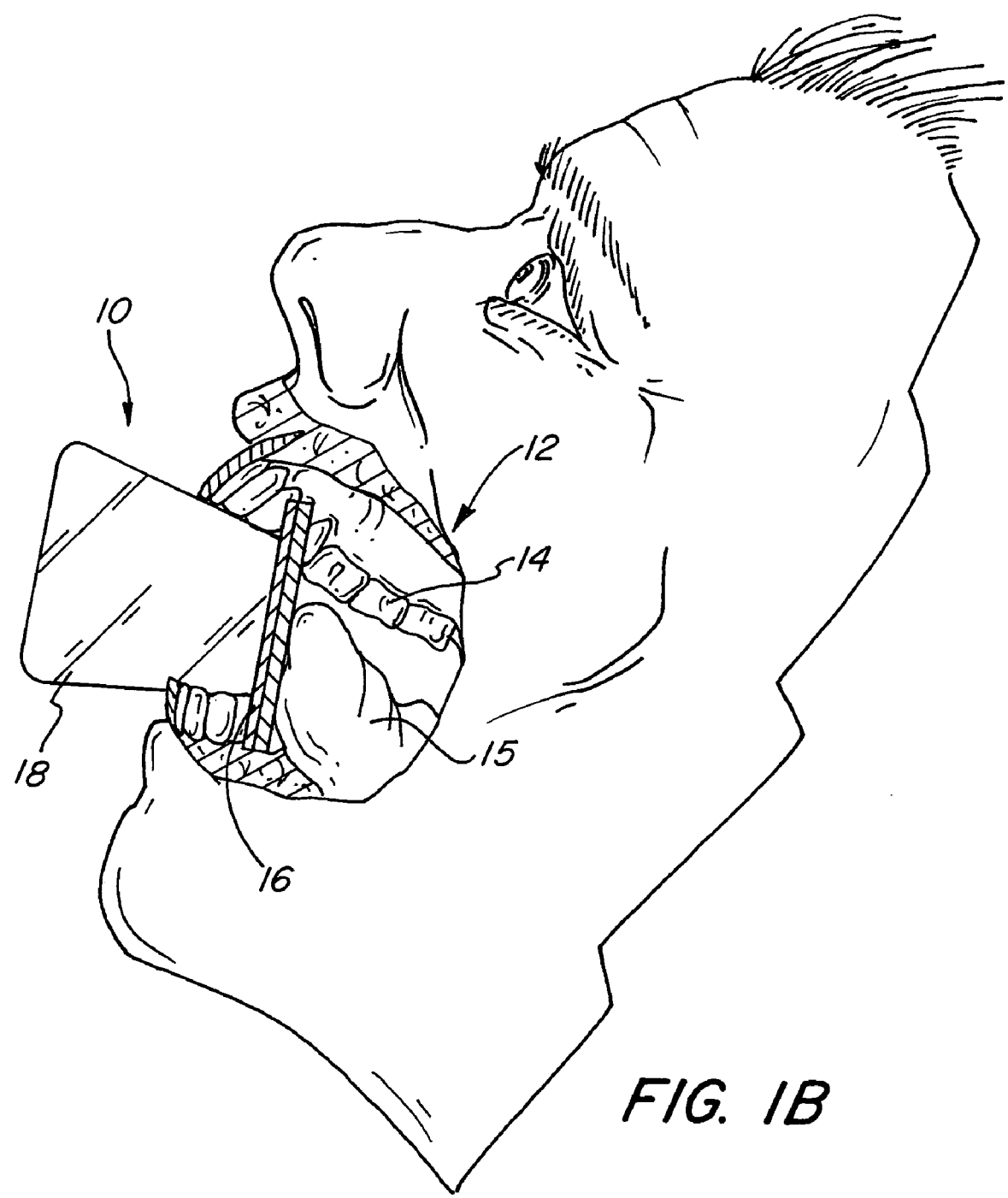
FIG. 1B is a cross sectional view taken along line 1B-1B in FIG. 1A illustrating placement of the present invention in a patient's mouth.

FIG. 1B illustrates a cross of an embodiment of the present invention placed in the mouth of a patient. The wings 18 are angled together so as to protect the patient's cheek and provide an isolated work area for the dental practitioner. The teeth 14 are separated by a portion of the wings 18 adjacent the body portion 16. The tongue 15 is retracted in the rear of the mouth in back of the body portion 16 preventing interference during the dental procedure.

Figure 2A:
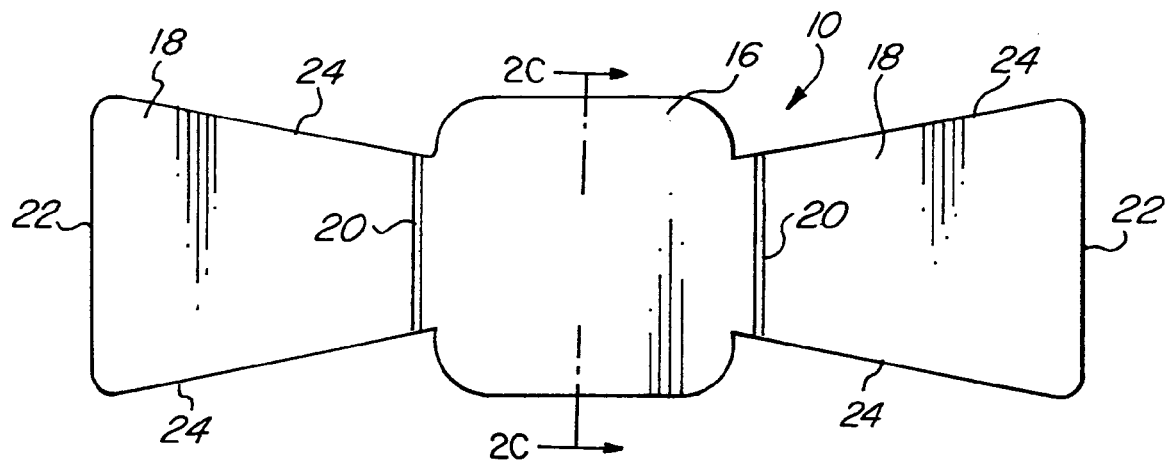
FIG. 2A is a back plan view of the present invention in a flat unfolded state.
Figure 2B:
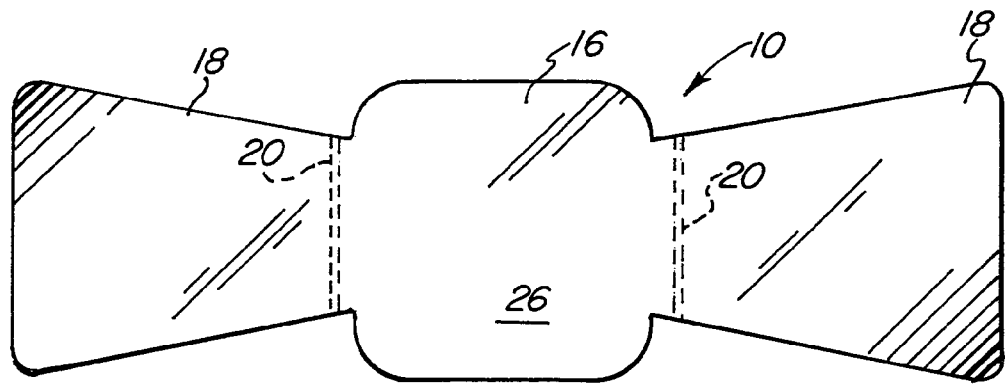
FIG. 2B is a front plan view of the present invention in a flat unfolded state.
Figure 2C:
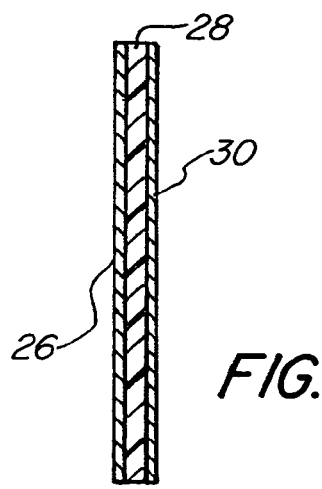
FIG. 2C is a cross section taken along line 2C-2C in FIG. 2B.

FIGS. 2A to 2C more clearly illustrate the shape and construction of an embodiment of the bite block 10 of the present invention. The bite block 10 in FIGS. 2A and 2B is illustrated in a flat or unfolded state. The bite block 10 comprises a composite sheet material having a generally rectangular center body portion 16 with opposing wings 18 attached to lateral sides of the generally rectangular center body portion 16. Adjacent the lateral sides are fold lines or scores 20. The wings 18 may be folded towards each other along the scores 20.

FIG. 2A illustrates the rear or back portion of the bite block 10. The wings 18 have an increasing lateral dimension or width extending to end edges 22 forming angled side edges 24.

FIG. 2B illustrates the front portion of the bite block 10 having a reflective or mirrored surface 26 on the body portion 16 and wings 18. The surface 26 may be a reflective white surface or an imaging mirrored surface. Preferably the surface is an imaging mirrored surface and provides a high quality image of the teeth as illustrated in FIG. 1A.

FIG. 2C is a cross section taken along line 2C-2C in FIG. 2A. FIG. 2C illustrates the composite structure of the bite block 10. A foam core 28 has a paper backing 30 on one side. On the other side is a highly reflective thin film material 26 used to form an image. This composite structure provides a strong inexpensive bite block 10.

Figure 3:
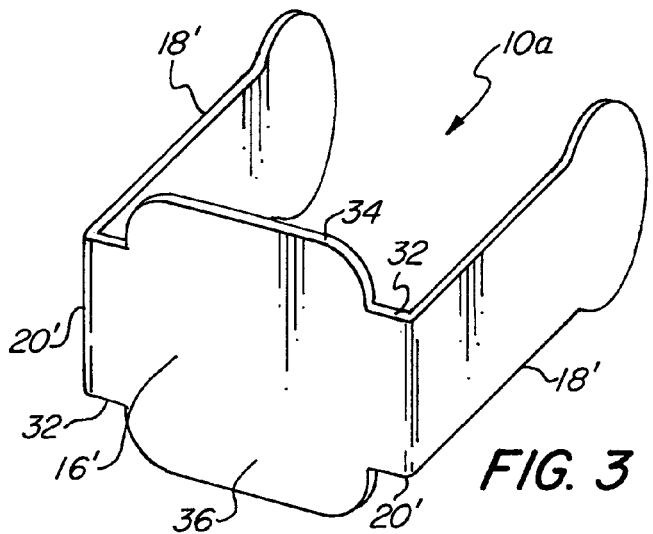
FIG. 3 is a perspective view of another embodiment of the present invention.
Figure 4A:
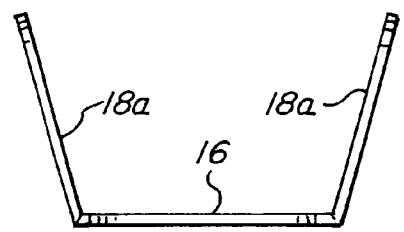
FIG. 4A-D are top plan views of different wing configurations.
Figure 4B:
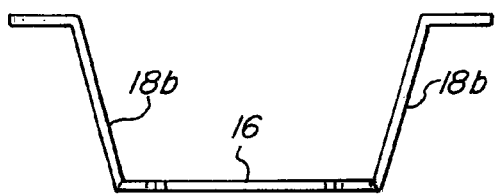
Figure 4C:
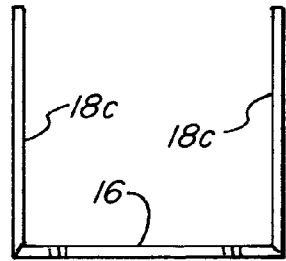

Another embodiment is show in FIG. 3. The device comprises a center body section 16' with two symmetrical saddles 32 on either side. The center body section 16' is disposed inside the mouth in the tongue region. Typically it can be placed from the mandibular first molar/second bicuspid area on one side of the mouth to the corresponding area on the other side of the mouth. The angle of placement with respect to the mouth opening, in all axes, can be adjusted depending on the access needed by the dental professional. The saddles 32 are placed so that one saddle 32 is on the left side of the open mouth and one on the right side of the open mouth. The upper and lower rows of teeth on one side will then bite down upon the top and bottom side of the saddle 32 respectively. The same is true for the opposite side of the mouth. Extending at an angle from the saddles 32 are wings 18' bent along score 20'. The body portion 16' has a top body portion 34 and a bottom body portion 36, which need not be symmetrical depending upon the application.

The general shape of an embodiment is shown in FIG. 3. The dimensions of the bite block 10a can generally be those needed to accommodate placement in the mouth and thus can conform to general human, or animal anatomy. Embodiments can be sized to fit various human mouth sizes, such as for children, adults, males, females, large, medium, small, etc. The positioning of or location of different fold lines or scores may provide size adjustable embodiments. The general shape of an embodiment can have the top or roof of the center body taper down to the saddle 32 on each side and correspondingly the bottom or floor taper up to the saddle 32 on each side. Embodiments can be made all from one material as a continuous piece of material or from several different materials. Edges can be square or rounded to provide for comfort. The taper angles from the center body 16' to the saddles 32 can be 90 degrees or some angle that provides for difference in height from the body to the saddle.

Typical dimensions for an embodiment may range from approximately a total length of 24 mm, width or height of 40 mm with a body portion of between 24 mm and 37 mm. Other ranges as suitable for use in a mouth can also be used. Thickness may vary between 0.60 mm to 4 mm depending on the rigidity and strength of the material used.

Materials used to construct embodiments can be from suitable biocompatible materials generally known for use in the mouth. Such materials can be, but are not limited to, plastics, cloth, poster board and/or other paper based products, canvas board, foam board, laminates, adhesives, metals such as stainless steel, aluminum, copper and other metals suitable for use in the mouth, and various combinations of all of the above listed materials. The materials can be chosen so embodiments are disposable. Alternatively materials can be chosen so that embodiments or parts thereof are able to be sterilized and re-used.

FIGS. 4A to 4D illustrate different shaped or angled wings. Body portion 16 may have obtusely angled wings 18a, bend end wings 18b, bent perpendicular wings 18c, or bent back wings 18d. The wings may be bent in a variety of shapes depending upon the application and need.

Figure 5:
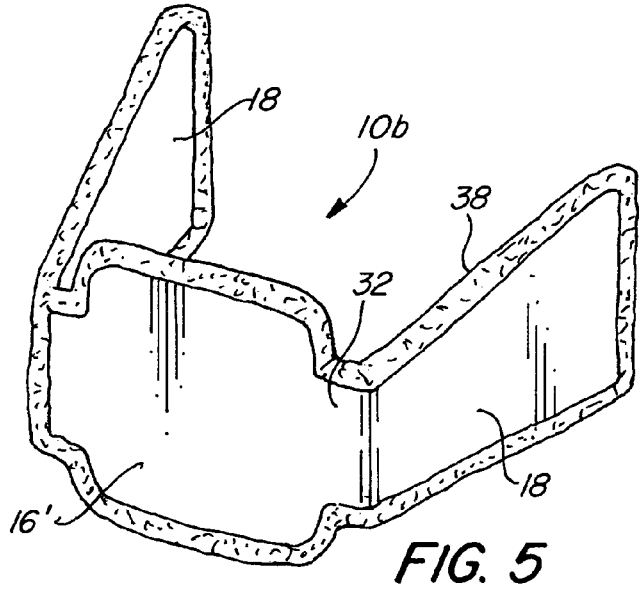
FIG. 5 is a perspective view of another embodiment of the present invention.
Figure 4D:
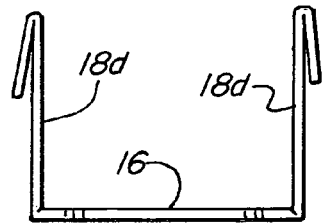

FIG. 5 illustrates another embodiment of a bite block 10b. In FIG. 5 a cushion 38 is illustrated placed around the perimeter or edges of the bite block 10b, including the body portion 16', wings 18, and saddles 32. The cushion 38 provides additional comfort to the patient and prevents chaffing. The cushion 38 may be made of any soft material, such as foam, cotton, or other equivalent material. The saddles can be covered in a compressive material or some type of cushioning covering such as foam, cork, cloth, paper, or rubber, to provide comfort to the patient.

Generally the dimensions of the wings are constrained only by the size of the patient's mouth. The wings can be flexible and if so, are attached in a way that allows them to be positioned at certain angles that provide for retraction to some degree of the upper and lower cheeks and lips.

FIGS. 6 to 9 illustrate different shapes for the wings. The wings can be straight or tapered or increasing in width. The wings can be wrapped or otherwise encased or partially encased in a compressible or other soft material such as rubber, cork, paper, or foam to make the wing more comfortable or to protect the tissue coming in contact with the wing such as the lips.

Figure 6:
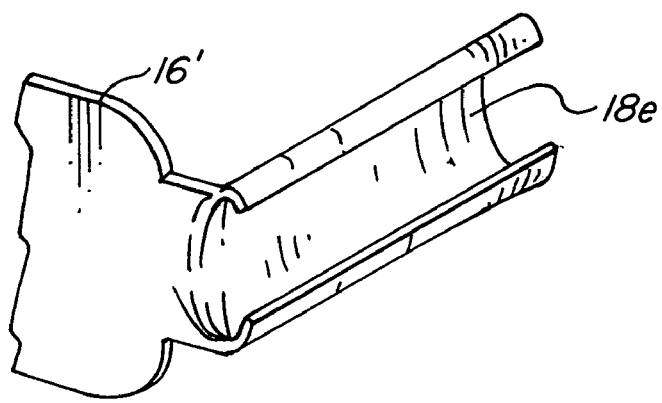
FIG. 6 is a schematic view illustrating a wing portion having a convex surface of an embodiment of the present invention.
Figure 7:
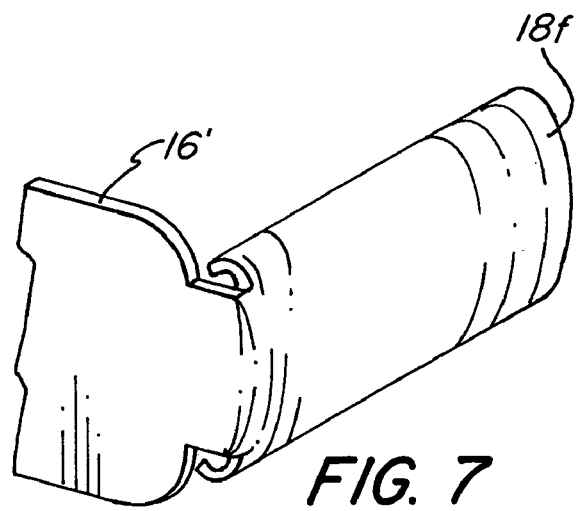
FIG. 7 is a schematic view illustrating a wing portion having a concave surface of an embodiment of the present invention.

FIGS. 6 and 7 illustrate the wings 18e and 18f attached to body portion 16' rolled over on themselves to some degree to provide a rounded edge. As illustrated in FIG. 6, the wing 18e may be concave in shape to catch and retract the upper and lower lips. As illustrated in FIG. 7, the wing 18f may be convex in shape.

Figure 8:
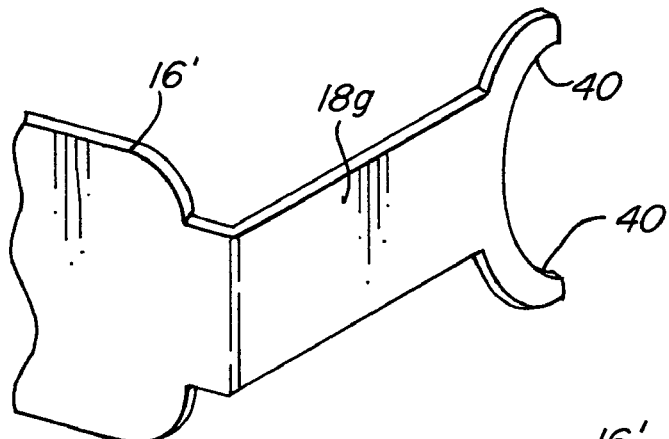
FIG. 8 is a schematic view illustrating a wing portion having bifurcated arms of an embodiment of the present invention.

FIG. 8 illustrates the ends of the wings 18g, the end opposite of the attachment point to the saddle, can be hollowed out or otherwise manufactured in a generally semi-circular or crescent shape to provide retraction arms 40 for retraction or holding of the upper and lower lips. The crescent shaped or semicircular parts can in certain embodiments be attachable or removable to the proximal ends of the wings to better fit the lips and retract them.

Figure 9:
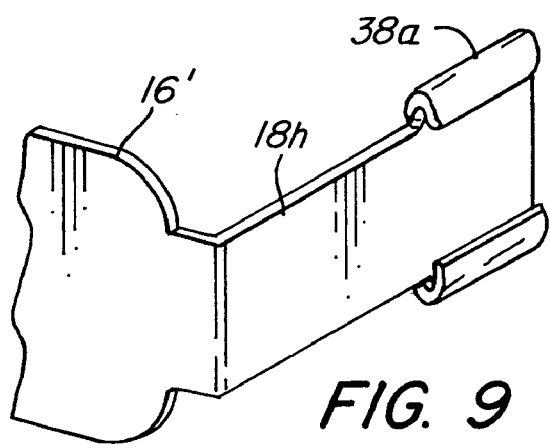
FIG. 9 is a schematic view illustrating a wing portion having a partial cushion material of an embodiment of the present invention.

FIG. 9 illustrates the end of the arms 18h having a portion covered in a cushion material 38a. The cushion material 38a can be foam, cork, rubber or other equivalent material and protects the lips and is more comfortable.

Figure 10:
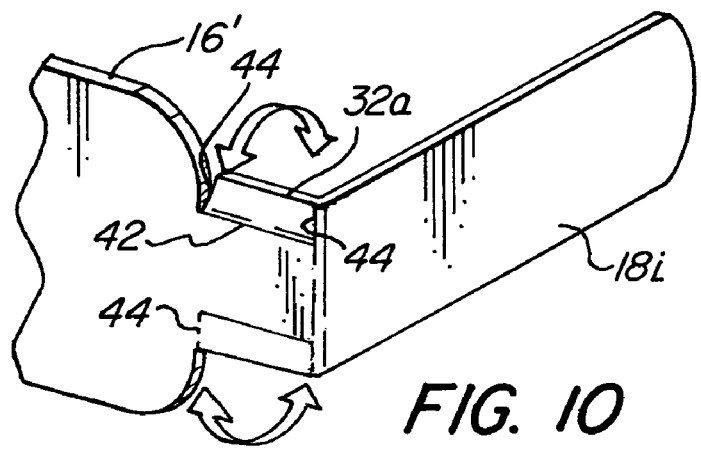
FIG. 10 is a schematic view illustrating a wing portion having an adjustable width of an embodiment of the present invention.
Figure 11:
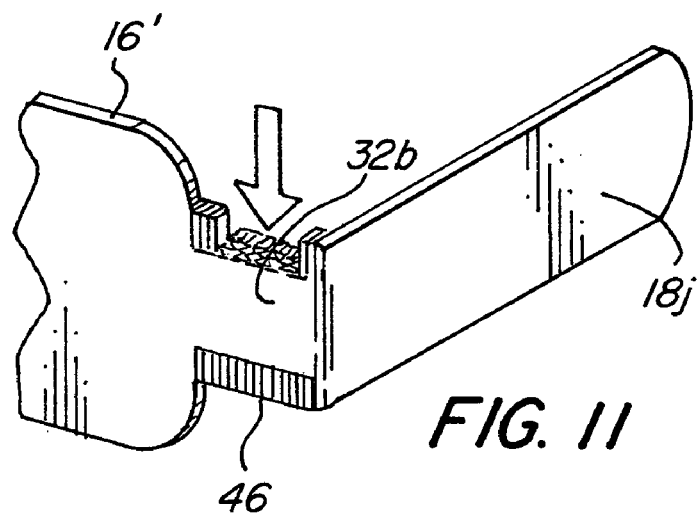
FIG. 11 is a schematic view illustrating a wing portion having a multiple cut portion for biting of an embodiment of the present invention.
Figure 12:
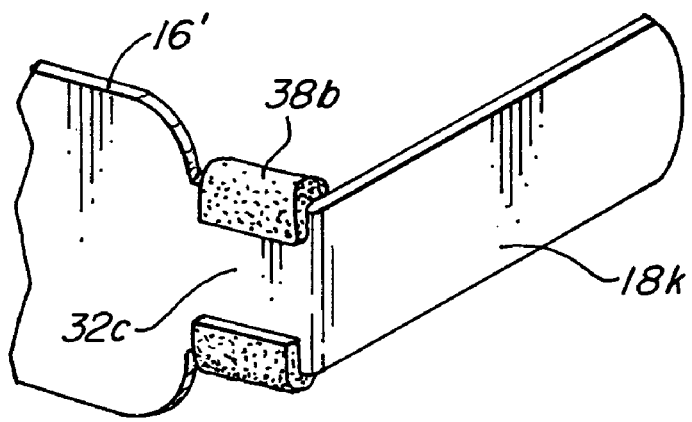
FIG. 12 is a schematic view illustrating a wing portion having a cushioned portion for biting of an embodiment of the present invention.

FIGS. 10 to 12 illustrate other embodiments having different types of saddles to provide adjustability or comfort. FIG. 10 illustrates a body portion 16' having a saddle portion 32a with a bite adjusting score 42 and a saddle cuts 44. Arm 18i is attached to the saddle portion 32a. The combination of the bite adjusting score 42 and the saddle cuts 44 permit the top portion of the saddle portion 32a to be bent over along the bite adjusting score 42. This provides a bite adjusting feature permitting adjustment of the distance between teeth depending upon the need.

FIG. 11 illustrates another embodiment providing cushioning. Attached to body portion 16' is a saddle portion 32b having a plurality of close cut fissures or cuts 46 formed in the top and bottom portions of the saddle portion 32b. Arm 18j is attached to saddle portion 32b. The close cut fissures or cuts 46 provide some give or compliance upon biting down providing a more comfortable bite block. Accordingly, the saddle 32b can be adjustable whereby the top and bottom of the saddle 32b, the top corresponding to the roof of the center body and the bottom corresponding to the floor of the center body, can be folded or otherwise rolled or bent to adjust the interocclusal or biting distance. This adjust can be made by the dental professional. Additionally, the patient can occlude or bite down into the saddle area and across the joint connecting the saddle and a wing, thus providing for a range of mouth sizes.

FIG. 12 illustrates a saddle portion 32c having a cushion 38b placed thereon. The saddle portion 32c is between the body portion 16' and the wing 18k. The cushion 38b provides additional comfort to the patient upon biting down.

During certain dental procedures it is desired that saliva and other fluids in the oral cavity such as blood or particulates from dental procedures be removed from the mouth. The mouth contains salivary ducts of the sub-mandibular and sub-lingual salivary glands which empty into the area between the base of the tongue and the lower front teeth. It may be desirable to remove this saliva or a portion of it, while using a bite block.

This unwanted amount of saliva, which can impede dental work and treatment, can be minimized just by the retraction of the tongue. The amount of saliva in the anterior floor of the mouth can be dictated by the tongue touching and stimulating certain glands or receptive cells which in turn cause saliva to flow, as well as the retraction if the tongue mechanically constricting salivary ducts. Embodiments of this bite block can be fitted with tubing that allows suction to be applied inside the mouth.

FIGS. 13 to 16 illustrate different embodiments of the invention providing moisture control.

FIG. 13 illustrates a tube attached to the center body portion 16' of a bite block 10c with holes or similar means to allow fluid to be suctioned out of the adjacent areas. This tubing or vacuum line 50 could be connected to the typical vacuum system present in a dental office. The tubing may be coiled. A non-coiled suction tube or vacuum line 50 is illustrated. The tube or vacuum line 50 is attached to a body extension 48. The body portion 16' has a partial mirrored surface 26' and attached wings 18'.

Additionally, saliva and other fluids or particulate removal can be accomplished without the aid of a vacuum or suction system. FIGS. 14 to 16 illustrate different embodiments using cotton rolls to control moisture.

FIGS. 14 illustrates bite block 10d having a cotton roll 52 attached to a body extension 48 extending from the body portion 16' Wings 18' extend from body portion 16'. The body portion 16' and attached wings 18' may have a reflective or mirror surface.

FIG. 15 illustrates bite block 10e having a cotton roll 56 having a longitudinal bore 58 sliding onto an arm 54 attached to the body portion 16' Wings 18' extend from body portion 16'. The body portion 16' and attached wings 18' may have a reflective or mirror surface.

FIG. 16 illustrates bite block 10f having indents 60 formed adjacent body portion 16' and wings 18' for receiving the outer circumference of cotton rolls 52.

As shown in FIGS. 14-16 cotton rolls, wafers, or other absorptive materials generally known in the art of dental procedures can be attached to the bite block, typically at the floor of the center body. Various methods can be used to hold these absorptive materials in place including the use of adhesives, notches in the center body, fingers or tongs in the floor of the center body, or a retaining center arm as shown in FIG. 15 to receive a roll with a hollow interior. Further, indentions can be used as additionally shown in FIG. 16.

In the present invention, the center body of the device typically provides for a tongue retraction feature due to its shape and placement. Generally, the tongue will be behind and press against the rear of the center body, with the center body placed between the tongue and the opening of the patient's mouth. Retracting the tongue can be useful in many dental procedures.

However, in certain cases, for example where the operator might wish to isolate the first or second molars and the tongue cannot be retracted far enough posteriorly for the bite block to be placed on the retro-molar pads, behind all teeth, it may be necessary to modify the bite block.

Figure 17:
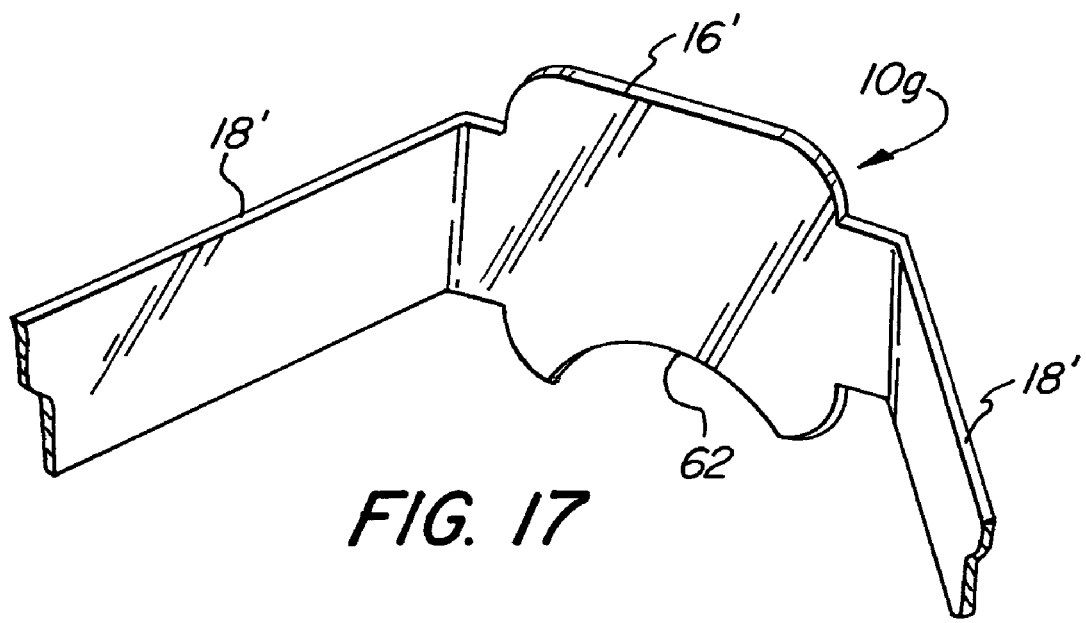
FIG. 17 is a schematic view illustrating another embodiment of the present invention having an opening formed in the body portion and adapted to be placed on the retro molar pads in the mouth.
Figure 18:
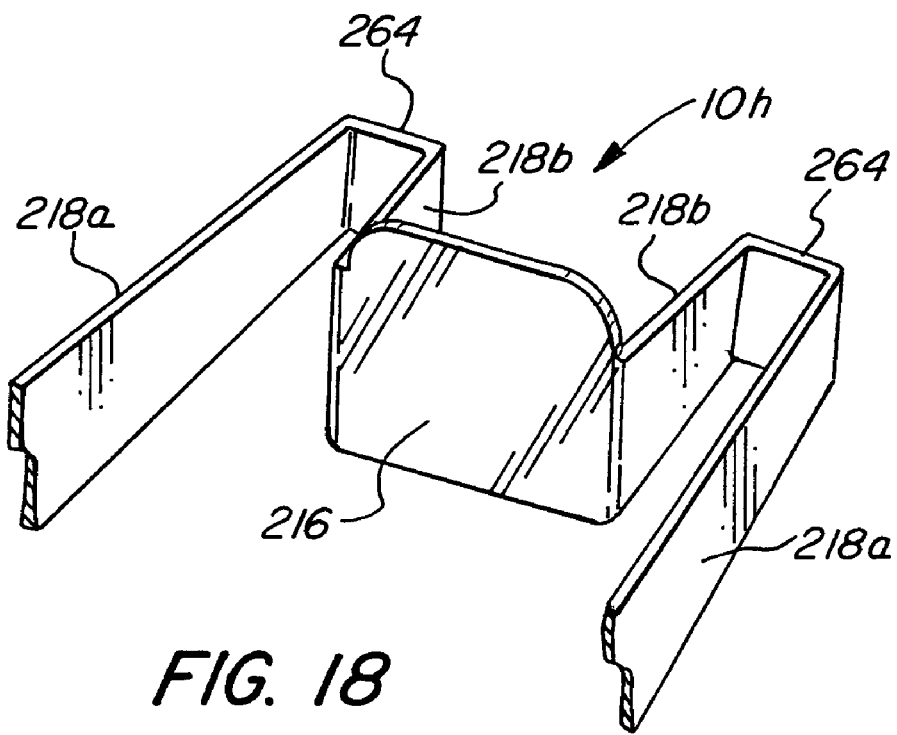
FIG. 18 is a schematic view illustrating another embodiment of the present invention adapted to be placed on the retro molar pads deep in the mouth.

FIGS. 17 and 18 illustrate bite blocks that can accommodate placement further back in the patient's mouth. The embodiments illustrated in FIGS. 17 and 18 do not fully retract the tongue.

FIG. 17 illustrates bite block log having a body portion 16' with a tongue opening 62 and longer wings 18'. The tongue opening 62 permit the tongue to pass through when the body portion 16' extends further into the mouth.

FIG. 18 illustrates another embodiment of a bite block for placement further back in the patient's mouth or on the retro-molar pads. Bite block 10h has multiple folds that permit partial tongue retraction. Body portion 216 has inside wings 218b extending from either side. A retro-molar portion 264 is placed between the inside wings 218b and outside wings 218a.

While certain preferred embodiments of a bite block of the present invention have been illustrated and described different combinations of features may be incorporated in different embodiments. Certain embodiments can include a mirror or otherwise reflective surface on all or part of the center body. Typically this surface would be mounted on the front facing portion of the center body so that when the bite block is placed inside a patient's mouth the lingual surfaces of the maxillary or mandibular anterior teeth and gingiva are shown via reflection to the dental professional. Use of a mirrored surface can reduce or eliminate the need to use an additional dental mirror while performing dental procedures. The mirror surface can generally be used with all or almost all of the embodiments described herein. Some dental professionals, dentists, or dental hygienists out-of-habit may wish to use their regular dental mirror in addition to the mirrored mouth prop device or bite block. This is fine as the device will reflect additional illumination as well as provide tongue retraction and a larger tongue-free working area with less moisture in addition to a stable opening of the mouth.

The mirrored surface can be made of materials which generally have a reflective quality and are biocompatible. These can be glass, regular or magnified, polished steel, reflective polymers such as acrylics, reflective metals and other materials generally known in the art to possess reflective characteristics.

Embodiments with or without a mirror can include an illumination source that provides light inside the mouth to assist the dental professional with viewing interior areas of the mouth. Such illumination source can be a light emitting diode (LED) or other light sources generally known in the art.

Generally, construction of the bite block can vary depending upon the different embodiments. The construction and materials may be all plastic; plastic with a thin adhesive mirror finish; regular manufactured mirror, typically film, about 0.2 mm thick and can be plastic; poster board or other paper product; poster board with a thin mirror film; canvas board; foam board; metals such as stainless steel, aluminum, copper, or other metals; or various combinations of all the above. Mirrors can be regular on one side and magnified on the opposite side. The wings can be bent to position the desired mirror to be used.

The different embodiments described herein can be used during the performance of dental procedures requiring access to the interior of the patient's mouth. In typical use, the patient will be instructed to place their tongue on the roof of the mouth and bite down gently, not as hard as you can, or some similar instruction.

While several embodiments can have tongue retraction capability, embodiments can also be manufactured with an opening for the tongue. This can allow the device to be placed more posteriorly, further back or posterior to the second molars or being placed on the retro-molar pads, without being limited to retracting the tongue. Also the bite block could be manufactured with a flexible "cross piece" which will permit this further backward placement in the mouth.

Use of different embodiments can provide an anchored mirror resulting in convenience in visibility as well as light reflection; dual mouth props; tongue retraction; cheek/lip retraction; moisture control; regular and magnified mirror vision.

Different embodiments may be used as mouth props. Embodiments used as mouth props or bite blocks can be with or without a mirrored center body piece. Biting down on two supporting structures simultaneously keeps the mouth open and can allow the patient to relax into the bite instead of having to make a conscious effort to remain open. Embodiments of this bilateral bite block can be placed relatively quickly and simply at once. Also, one side braces against the opposite side for additional stability and comfort. Embodiments of the bilateral bite block can be disposable. Embodiments can be above or below the tongue, can or can't retract the tongue; can be used on top of a rubber dam if needed; can be used with or without an attached mirror. Embodiments can be used for anterior endo, upper or lower. As the device is not unilateral, stress on muscles is distributed approximately evenly.

Different embodiments may be used as a tongue retractor. Embodiments provide for intraoral tongue retraction or fixation so the operator will not be so encumbered by extra oral supports, and thus can utilize the benefits of tongue retraction more freely. The use for tongue retraction also helps to keep the lower lingual anterior area of the mouth drier. Tongue retraction can keep the tongue out of the way allowing for a much larger working space in the lower anterior area, lower front area of the mouth. Tongue retraction embodiments of the invention are typically comfortable to the patient, easy to place, no real extra-oral parts to contend with, is a much more stable, and the operator doesn't have to stand there and hold a retractor. Additionally, embodiments of the invention do not substantially move when the patient swallows.

When the tongue is retracted, there is less flow of saliva in this area, floor of the mouth. Movement of the tongue, in the floor of the mouth, may stimulate salivary gland receptors resulting in saliva secretion. When the tongue is retracted and this movement prohibited, there can be less saliva flow. Embodiments of the invention provide, if needed, a fairly stable surface for attaching suction or cotton rolls or cotton wafers to the back of the device, or extending out towards the front of the floor of the device. This can be helpful in the area of the sub lingual salivary ducts and the submandibular salivary ducts. A soft cotton roll or wafer, attached to the bottom of this device, can rest directly on these ducts with very gentle pressure.

Embodiments of the invention also aid in visibility. Embodiments with a mirror can, by having the patient open just very slightly then closing, easily tilt the mirror device up-and-down giving a good view of the lingual surfaces of either the upper of lower anterior teeth. But also, by this same method, user can tilt the mirror device from side-to-side giving a wider range view of the linguals of the bicuspids and also the first molars, maxillary and mandibular, upper and lower arches/teeth. A doubled-sided mirror can have a regular side or unit magnification on a front or one side and a magnified side on the other side or back, or vice versa. The wings can be bent to face either direction so that either mirror surface can be used as desired.

The mirror can be attached or otherwise affixed to the center body piece or other components of the bite block, or can be integrally contained in the bite block; for instance when the bite block is comprised of materials that are reflective by nature and do not require the addition of a reflective surface. Mirror surfaces can also be attached to the wings themselves for additional vision or illumination. Mirrors can be made of thin film. Mirrors can be made of plastic material or acrylic sheet, sold under the trademark Plaskolite, of about 0.060 inch or about 0.080 inch or about 0.2 mm or about 1 and ½ mm.

Because the anchored mirror can have two surfaces, the mirror's front surface can be regular or unit magnification and the reverse magnified. The wings in this double-sided mirror device can bend forward or backward, anteriorly or posteriorly, depending on which side of the mirror is being utilized.

Embodiments with an attached mirror can be used for many dental procedures. For example, the invention with a mirror may be used in the placement of lower or upper anterior lingual splints. The main purpose of a splint is to re-enforce teeth by joining them together to protect them from becoming any looser. Splints must be adjusted to and fastened to the teeth and are used most commonly on the lower front area, almost always from the tongue or lingual side which can be a very difficult area to see. Without use of the present invention, it was necessary to hold a regular dental mirror with one hand. The present invention may also be used for placement and cementation of lower or upper orthodontic retainers; placement of pit and fissure sealants; or packing lingual retractor cord under gingival tissue prior to taking an impression for such as a crown.

Tongue retraction helps keep this area dry, the mirror provides vision and illumination and the mirror also allows for the freedom of both hands. The present invention may also be used for viewing and placing implants and providing a good lingual view, increased illumination. For endodontic procedures on lower or upper anterior teeth embodiments of the invention can provide a view of the lingual entrance as well as help with a dry field. Dentists usually use a rubber dam in these situations but embodiments of the invention can also be used with or without a rubber dam in place. The present invention may also be used for placement of endodontic posts, once regular endodontics has been completed. Use of the present invention may also benefit periodontal surgery on lower or upper anterior teeth, particularly in grafting where both hands are needed.

For patient education an embodiment having a mirror can demonstrate to the patient where most calculus forms and the need for flossing or other care. The patient may then understand where most scaling will be done. The patient may also be shown in a post procedure view the result of calculus removal. The embodiment of the present invention having a mirror aids the dental professional's vision in scaling of this lower anterior area. This is especially helpful in that eighty percent of the calculus in the entire mouth accumulates on the lingual surface of these lower six anterior teeth. The invention also helps retract active, large muscular tongues and helps reflect light to the area. This mirror and also retraction of the tongue will allow the dental professional to work from behind and slightly to the side of the patient and, with the illumination from the mirror, the dental professional can scale these teeth with direct vision. This will also help with the use of an ultrasonic cleaner, as the dental professional will have a hand free to hold or move a suction tip around if needed.

The present invention with a mirror also helps in probing the gingiva that can be seen in the mirror. The dental professional will not have to pick up the regular mouth mirror nearly as much to check and record the markings on a probe. The dental professional can just probe and record, speeding up the recording procedure. Effort to improve this procedure with a probe-ballpoint pen has been developed to prevent having to pick-up a mirror and a pen and a probe each time after recording the pocket depth. The present invention may also be used during composite resin polymerizing curing through reflection of a curing light into hard to get to areas with the bulky curing light tip, such as in the lower anterior lingual areas near the floor of the mouth. The mirror will allow more thoroughly curing the materials in these areas which are difficult to access with the relatively blunt nose of the curing light, including an LED curing light.

Also different embodiments will help by keeping lips and cheeks further out of the way. This will aid in all the uses indicated above, but will additionally provide intraoral cheek and lip retraction. Wings of the invention can also be used to position or move a device and to prevent it from being swallowed. Embodiments of the invention can provide lip or cheek retraction for aesthetic procedures such as placement of multiple veneers and placement of multiple orthodontic brackets and appliances where the mouth and its tissues must be especially open, dry, and accessible. Embodiments of the invention can be useful in conjunction with dental photography including of lingual areas.

The present invention may have many other uses, such as use by the patient at home or other locations other than a dental office in conjunction with scalers. Since the tongue surfaces of the lower anterior teeth are typically the most prevalent in accumulation of calculus, and cannot normally be seen by the patient, embodiments of the invention can be of assistance. Additionally, an embodiment of the invention can comprise an advertisement imprinted on the back or front of the device.

While the present invention has been described with respect to several embodiments, it will be understood that various modifications may be made without departing from the spirit or scope of the invention.

What is claimed is:

1. A bilateral bite block comprising:
   an initially flat sheet material;
   a flat central portion formed in said initially flat sheet material having opposing ends;
   a readily flexible wing formed in said initially flat sheet material integrally attached to each of the opposing ends of said central portion said readily flexible wing capable of being selectively bent by hand and said readily flexible wing and central portion sized to extend between bilateral upper and lower rows of teeth, with said readily flexible wings having a length adapted to extend out of a patient's mouth when positioned therein, and
   a mirror placed on said central portion,
   whereby said readily flexible wings may be bent by hand and positioned for propping the mouth of a patient open and extend out of the patient's mouth permitting easy positioning during a dental procedure.

2. The bilateral bite block as in claim 1 wherein:
   said central portion and said readily flexible wings comprise a composite material having a foam core.

3. The bilateral bite block as in claim 1 further comprising:
   a fold line placed adjacent each of the opposing ends of said central portion,
   whereby said readily flexible wings may be bent towards each other.

4. The bilateral bite block as in claim 1 wherein:
   said readily flexible wings increase in a lateral dimension extending from said central portion.

5. A bilateral bite block comprising: a flat sheet of flexible material having a central body portion and a pair of wings, each wing of said pair of wings having an increasing lateral dimension extending outward from the central body portion, whereby when the bilateral bite block is placed inside a patient's mouth each wing of the pair of wings extends outside of the patient's mouth facilitating easy positioning and removal of the bilateral bite block; and
   a mirror placed on at least one surface of said flat sheet,
   a fold line placed between each wing of said pair of wings and said central body portion,
   whereby said pair of wings may be selectively folded by hand towards each other for positioning within the mouth of a patient.

6. The bilateral bite block as in claim 5 wherein:
   said flat sheet comprises a composite structure having a foam core.

7. The bilateral bite block as in claim 5 wherein: said mirror comprises a thin film mirror.

8. The bilateral bite block as in claim 5 further comprising:
   a saddle portion having a smaller lateral dimension than the central body portion placed between the central body portion and each wing of the pair of wings.

9. The bilateral bite block as in claim 5 further comprising:
   means, placed on edges of said flat sheet, for cushioning.

10. The bilateral bite block as in claim 9 wherein:
    said means for cushioning comprises a plurality of cuts.

11. The bilateral bite block as in claim 5 wherein:
    the increasing lateral dimension extends in a straight line outward from the central body portion.

12. A bilateral bite block for use in a dental procedure comprising:
    a flat composite sheet material having opposing planar surfaces comprising a backing, a reflective material covering an entire surface of one of the opposing planar surfaces of said flat composite sheet material, and a foam core separating the backing and the reflective material, said flat composite sheet material having a central body portion and a pair of adjacent wing portions, each wing portion of the pair of adjacent wing portions integrally formed on a side of said central body portion and having an increasing lateral dimension extending in a straight line from said central body portion to an end thereof forming angled side edges with respect to a longitudinal axis of the pair of wing portions, the central body portion and the pair of wing portions having a symmetrical shape along both the longitudinal axis and a lateral axis;
    whereby when the bilateral bite block is placed inside a patient s mouth each wing portion extends outside of the patient s mouth facilitating easy positioning and removal of the bilateral bite block; and
    at least two fold lines formed on the backing, one each of said at least two fold lines formed between the central body portion and the wing portion of the pair of adjacent wing portions,
    whereby each wing portion of said pair of adjacent wing portions is selectively bent by hand towards the central body portion and positioned in the mouth of a patient for propping open the mouth of the patient and providing improved visibility due to the reflective material.

13. The bilateral bite block for use in a dental procedure as in claim 12 further comprising:
   means, placed on edges of said composite sheet material, for cushioning.

14. A disposable bilateral bite block made of composite flat sheet material comprising:
   a flat composite sheet material having opposing planar surfaces comprising; a paper backing; a foam material attached to said paper backing; a reflective thin film material covering an entire surface of one of the opposing planar surfaces and attached to said foam material;
   said paper backing, foam material, and reflective thin film material laying in a plane and cut in a shape forming a body portion and wings on opposing ends of the body portion, each of the wings having an increasing lateral dimension extending from the body portion;
   whereby when the bilateral bite block is placed inside a patient's mouth each wing extends outside of the patient's mouth facilitating easy positioning and removal of the bilateral bite block; and
   a fold line formed in the flat composite sheet material between the body portion and each of the wings, wherein each of the wings is capable of being folded by hand about said fold line towards each other out of the plane so that the wings can be positioned in a patient's mouth with each wing folded to a positioned between upper and lower rows of teeth, with one wing positioned on each side of the patient's mouth,
   whereby the patient's mouth is held open during a dental procedure.

15. The disposable bilateral bite block made of flat composite sheet material as in claim 14 further comprising:
   a plurality of closely spaced cuts extending from an edge and formed in each wing adjacent the body portion,
   whereby said plurality of closely spaced cuts provide compliance upon biting down.

* * * * *